United States Patent [19]
De La Mata et al.

[11] Patent Number: 5,417,665
[45] Date of Patent: May 23, 1995

[54] INTRAVASCULAR CANNULA

[75] Inventors: Carlo R. De La Mata, North Miami Beach; Luis A. Davila, Cooper City, both of Fla.

[73] Assignee: Cordis Corporation, Miami Lakes, Fla.

[21] Appl. No.: 138,801

[22] Filed: Oct. 19, 1993

[51] Int. Cl.⁶ .......................................... A61M 5/178
[52] U.S. Cl. ..................................... 604/164; 604/53; 604/264; 604/280
[58] Field of Search ................. 128/656, 657, 658; 604/53, 170, 264, 280, 282, 164; 606/194

[56] References Cited

U.S. PATENT DOCUMENTS

| | | | |
|---|---|---|---|
| 4,629,450 | 12/1986 | Suzuki et al. | 604/164 |
| 4,898,591 | 2/1990 | Jang et al. | 604/282 |
| 4,944,729 | 7/1990 | Buckberg et al. | 604/264 |
| 4,950,257 | 8/1991 | Hibbs et al. | 604/264 |
| 5,066,285 | 11/1991 | Hillstead | 604/164 |
| 5,116,323 | 5/1992 | Kreuzer et al. | 604/280 |

Primary Examiner—C. Fred Rosenbaum
Assistant Examiner—N. Kent Gring
Attorney, Agent, or Firm—Gerstman, Ellis & McMillin, Ltd.

[57] ABSTRACT

An intravascular catheter comprises a plastic tube of a diameter capable of occupying a blood vessel. The plastic tube defines a tapered distal tip. The distal tip comprises an annular, distal end portion having an outer diameter that tapers at a first acute angle to the tube longitudinal axis, distally and inwardly to a thin, annular, distal end surface. The tube also defines a second, tapered, annular portion proximal of and next to the annular, distal end portion. The second portion defines an outer diameter that tapers distally and inwardly down to an outer diameter of essentially no less than the maximum outer diameter of the annular, distal end portion. The second portion tapers at a second acute angle to the longitudinal axis, which is less than the first acute angle. Also, an improved composition for the cannula tube is disclosed.

19 Claims, 1 Drawing Sheet

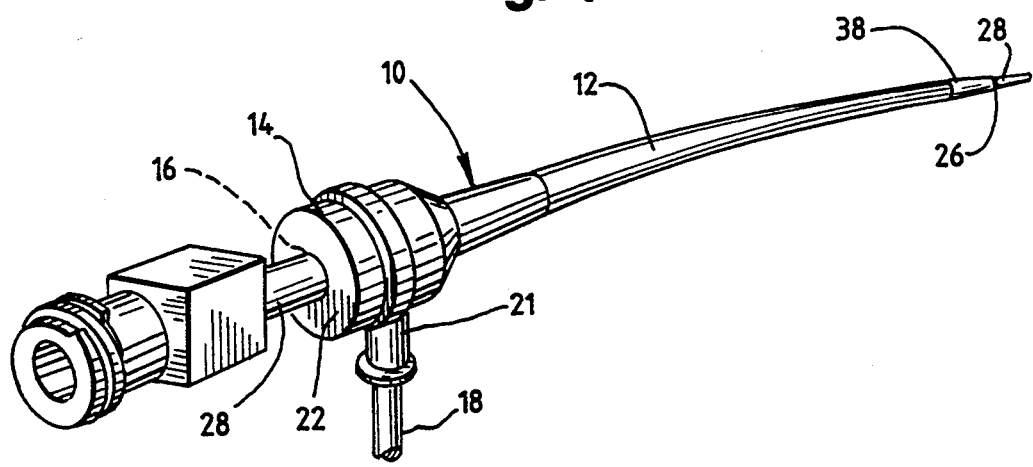
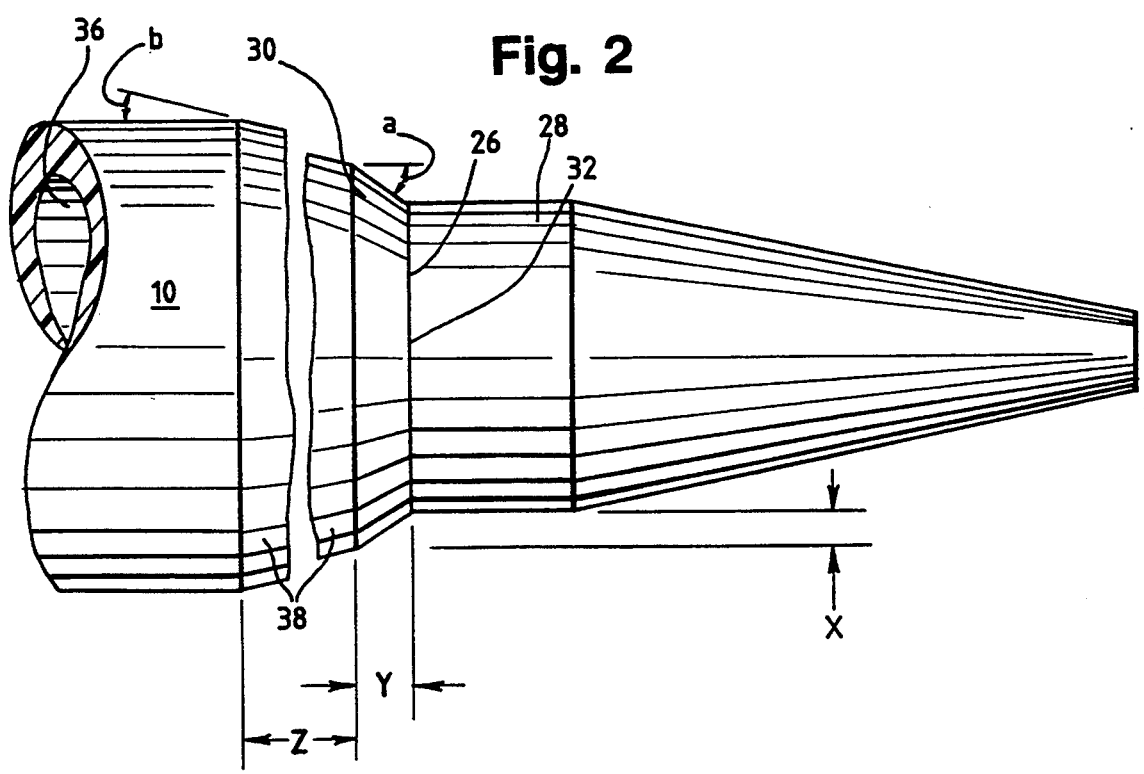

INTRAVASCULAR CANNULA

BACKGROUND OF THE INVENTION

Catheter sheath introducers are well-known and in clinical use, comprising an intravascular cannula which carries a proximal hub. The hub, in turn, carries a slit elastomer partition valve through which a catheter or a guidewire can penetrate to provide sealing advancement through the cannula of the catheter sheath introducer. Also, it is typical for a branch line to connect with the hub and the interior of the cannula for flushing, and for obtaining blood samples, as the cannula of the catheter sheath introducer occupies a position penetrating through the skin and the wall of an artery to reside in the artery. Thus, catheters can then be advanced and withdrawn through the catheter sheath introducer, while minimizing further injury to the patient above and beyond the single emplacement of the catheter sheath introducer through the skin and artery wall.

Catheter sheath introducers are typically advanced through the skin and an artery wall while a penetrating stylette (also called a "dilator") occupies the lumen of the catheter sheath introducer cannula. The stylette penetrates through the skin and artery wall, taking the catheter sheath introducer with it.

However, difficulties are encountered because the cannula of the catheter sheath introducer naturally has a wall thickness, resulting in a distal end which causes resistance to advancement of the stylette and catheter sheath introducer through the skin and the artery wall.

In accordance with this invention, an intravascular cannula is provided which has a distal tip that greatly reduces resistance of the cannula to advancement through the skin and into an artery while positioned about a stylette. By this, tissue damage and difficulty of emplacement of such an intravascular cannula can be greatly reduced.

DESCRIPTION OF THE INVENTION

In accordance with this invention, an intravascular cannula is provided which comprises a plastic tube of a diameter capable of occupying a blood vessel. The plastic tube defines a tapered, distal tip. The distal tip comprises an annular, distal end portion having an outer diameter that tapers at a first acute angle to the tube longitudinal axis, tapering distally and inwardly to a thin, annular, distal end surface.

The plastic tube also defines a second, tapered, annular portion which is proximal of and next to the annular, distal end portion, typically being in abutting relation thereto without an intervening cylindrical space portion of the cannula, although such a space portion may be provided if desired. The second portion defines an outer diameter that tapers distally and inwardly down to an outer diameter which is essentially no less than the maximum outer diameter of the annular, distal end portion. This second, tapered, annular portion tapers at a second acute angle to the cannula longitudinal axis which is less than the first acute angle of the annular, distal end portion.

Typically, the first acute angle ranges from 30 to 60 degrees, while the second acute angle ranges from 3 to 20 degrees.

The cannula of this invention is preferably made of a plastic having a Shore D durometer of 65 to 75, a flexural modulus of 60,000 to 70,000 lb./in$^2$, an elongation to break of about 350 to 550, a tensile yield strength of essentially 2500 to 3500 psi, and a tensile strength to break of essentially 7500 to 9000 psi. Typically, the plastic used may be nylon, particularly of the polyether block polyamide type, sold for example by Ato Chem. North America under the trademark Pebax. Specifically, Pebax 7033 may be used having a break tensile strength of about 8300 psi, an elongation to break of about 400%, a Shore D Durometer of about 69, and a flex modulus of 67,000 lb./in$^2$. This plastic is filled with a filler such as bismuth subcarbonate in a concentration of 10 to 20 weight percent, typically 15 percent, or barium sulphate in a concentration of 20 to 40 weight percent, typically 30 percent.

Also, the thin, annular, distal end surface of the cannula of this invention preferably has a wall thickness of essentially about 0.007 inch at the thickest, tapering down to a feather edge at the rip.

Such a cannula as is described herein may be carried about a dilator wire or stylette which occupies the lumen of the cannula, with the dilator wire having a tapered tip extending distally out from the cannula distal tip. Such a system may be advanced through the skin and an arterial or venous wall of the patient to occupy a blood vessel, with the advancement being accomplished with significantly reduced force, which significantly facilitates the process and reduces localized tissue injury.

DESCRIPTION OF THE DRAWINGS

FIG. 1 is a perspective view of a catheter sheath introducer made in accordance with this invention, shown with a stylette or dilator in the desired position for insertion of a distal portion of the catheter sheath introducer into the artery of a patient; and FIG. 2 is an enlarged, fragmentary plan view of the distal tip of the cannula and dilator stylette of FIG. 1.

DESCRIPTION OF SPECIFIC EMBODIMENTS

Referring to the drawings, a catheter sheath introducer 10 for penetration of an artery is shown. The catheter sheath introducer then serves as an entrance site for other catheters and guidewires, for example catheters for angiography and angioplasty.

Catheter sheath introducer 10 comprises a semi-flexible, self-supporting plastic cannula 12 which carries a hub 14 on its proximal end. Hub 14, in turn, carries an elastomeric partition 22 having a slit 16 therethrough, permitting the penetration of dilator stylette 28, as shown in FIG. 1, in which dilator stylette 28 passes through the slit 16 in diaphragm 22, extending through hub 14 and the entire lumen of cannula 12, past the distal end 26 of cannula 12, with a tapered point of the stylette penetrating outwardly from distal end 26.

As described above, catheter sheath introducer 10 and stylette 28 are of conventional design, apart from this present invention. Hub 14 also typically carries a side branch 21, which can connect to a fluid flow line 18 for receiving flushing solution and transferring it to the lumen of cannula 12, as well as for the taking of blood samples and the like.

Referring particularly to FIG. 2, in accordance with this invention, cannula 12 comprises a plastic tube which has a tapered, annular, distal end portion 30. Annular distal end portion 30 defines a typically feather edge tightly surrounding stylette 28, the feather edge typically having a thickness of about 0.0001 to 0.001 inch at annular end surface 32. Tapered distal tip portion 30 extends proximally back from end surface 32, having an outer diameter that tapers at an angle of about 30° to 60° to the tube or cannula longitudinal axis 34, this angle a being previously described as the "first acute angle". Specifically, this angle may be 45°. Distance Y—Y may be about 0.004 inch. Distance X—X may be about 0.004 inch.

The inner wall defining lumen 36 of cannula 12 is typically cylindrical and of a dimension to loosely accommodate stylette 28, so that stylette 28 may be inserted and withdrawn from cannula 12.

The distal end area of cannula 12 also defines a second, tapered, annular portion 38 which is positioned proximal of and next to annular, distal end portion 30. Here also, second portion 38 defines an outer diameter that tapers distally and inwardly down to a minimum outer diameter 40 which is essentially no less than the maximum outer diameter of annular distal end portion 30, the two sections abutting each other in this preferred embodiment. This second portion 38 tapers at a second acute angle b to longitudinal axis 34 of about 5° to 20°, which second acute angle b is less than the first acute angle of taper found in section 30. Specifically, the second angle may be about 7°, and distance Z—Z may be 0.046 inch. Preferably, distance Z—Z is about 8 to 15 times the length of distance Y—Y.

The sections of cannula 12 which are proximal to second tapered portion 38 are typically substantially cylindrical until the area of hub 14 is reached.

When the catheter sheath introducer 10 of this invention, carried on dilator cannula 28, is advanced, typically along a guidewire through the skin, the skin of course is substantially stretched at the entry site, first by the tapered configuration of the distal tip of stylette 28, and then followed by the respective annular tapers of sections 30 and 38. The ease of such penetration in accordance with this invention has been found to be significantly improved over corresponding cannulas of the prior art, with dramatically reduced insertion resistance force being found with this invention.

Typically, the wall thickness of cannula 12 apart from the taper is about 0.007 inch. In this specific embodiment of a catheter sheath introducer, the length of cannula 12 typically may be from about 10 to 105 cm.

Intravascular cannulas of the type disclosed may have thin walls with excellent kink resistance, coupled with a non-flaring distal tip, as is desirable. The cannula made of such material shows improvements in these characteristics over prior art materials such as nylon 12.

The above has been offered for illustrative purposes only, and is not intended to limit the scope of the invention of this application, which is as defined in the claims below.

That which is claimed is:

1. An intravascular cannula which comprises a plastic tube of a diameter capable of occupying a blood vessel, said plastic tube defining a tapered, distal tip, said distal tip comprising an annular, distal end portion having an outer diameter that tapers at a first acute angle to the tube longitudinal axis distally and inwardly to a thin, annular, distal end surface, said tube also defining a second, tapered, annular portion proximal and immediately of adjacent to said annular, distal end portion, said second portion defining an outer diameter that tapers distally and inwardly down to an outer diameter of essentially no less than the maximum outer diameter of said annular distal end portion, said second portion tapering at a second acute angle to said longitudinal axis which is less than said first acute angle.

2. The cannula of claim 1 in which said first angle is 30° to 60°.

3. The cannula of claim 1 in which said second angle is 5° to 20°.

4. The cannula of claim 1 in which said second portion is 8 to 15 times the length of the first portion.

5. The cannula of claim 1 in which said plastic is polyether block polyamide filled with 10 to 20 weight percent of bismuth subcarbonate.

6. The cannula of claim 1 which is an arterial catheter sheath introducer.

7. The cannula of claim 1 in which said thin, annular, distal end surface has a wall thickness of essentially 0.0001 to 0.001 inch.

8. The cannula of claim 1, in combination with a dilator wire stylette occupying the lumen of said cannula, said dilator wire stylette having a tapered tip projecting distally from said cannula distal tip.

9. An intravascular cannula which comprises a plastic tube of a diameter capable of occupying a blood vessel, said plastic tube defining a tapered distal tip, said distal tip comprising an annular, distal end portion having an outer diameter that tapers at a first acute angle of 30° to 60° to the tube longitudinal axis, distally and inwardly to a thin, annular, distal end surface, said tube also defining a second, tapered, annular portion proximal of and abutting said annular, distal end portion, said second portion defining an outer diameter that tapers distally and inwardly down to an outer diameter of essentially no less than the maximum outer diameter of said annular distal end portion, said end portion tapering at a second acute angle of 3° to 20° to said longitudinal axis which is less than said first acute angle.

10. The cannula of claim 9 in which said tube is made of a plastic having a Shore D durometer of essentially 65 to 75.

11. The cannula of claim 10 in which said plastic is a polyether block polyamide filled with 10 to 20 weight percent of bismuth subcarbonate.

12. The cannula of claim 11 in which said thin, annular, distal end surface has a wall thickness of essentially 0.0001 to 0.001 inch.

13. The cannula of claim 12 in combination with a dilator wire stylette occupying the lumen of said cannula, said dilator wire stylette having a tapered tip projecting distally from said cannula distal tip.

14. An arterial catheter sheath introducer which comprises a plastic tube of a diameter capable of occupying a blood vessel, a proximal hub carried on an end of said tube, a slit elastomeric partition valve carried in said hub, permitting an elongated member to penetrate through the entire length of said catheter sheath introducer without back leakage of fluids through said catheter sheath introducer, said tube being made of a plastic having a Shore D durometer of essentially 65–75, a break tensile strength of 7500 to 9000 psi, and an elongation to break of 350–550.

15. The cannula of claim 14 in which said plastic is filled with 10 to 20 weight percent of bismuth subcarbonate.

16. The catheter sheath introducer of claim 15 in which said cannula defines a thin, annular, distal end surface having a wall thickness of essentially 0.0001 to 0.001 inch.

17. The catheter sheath introducer of claim 14, in combination with a dilator wire stylette occupying the lumen of said cannula, said dilator wire stylette having a tapered tip projecting distally from said cannula distal tip.

18. The catheter sheath introducer of claim 14 in which said plastic is a polyether block polyamide.

19. The catheter sheath introducer of claim 15 in which said plastic is a polyether block polyamide.

* * * * *